United States Patent
Burgo

(10) Patent No.: US 11,229,589 B2
(45) Date of Patent: Jan. 25, 2022

(54) NATURAL HYDROCARBON/ESTER COMPOSITIONS WITH IMPROVED SENSORY PROPERTIES, FORMULATIONS AND RELATED METHODS

(71) Applicant: Inolex Investment Corporation, Wilmington, DE (US)

(72) Inventor: Rocco V. Burgo, Mullica Hill, NJ (US)

(73) Assignee: INOLEX INVESTMENT CORPORATION, Wilmington, DE (US)

( * ) Notice: Subject to any disclaimer, the term of this patent is extended or adjusted under 35 U.S.C. 154(b) by 0 days.

(21) Appl. No.: 16/176,942

(22) Filed: Oct. 31, 2018

(65) Prior Publication Data
US 2019/0269587 A1    Sep. 5, 2019

Related U.S. Application Data

(60) Provisional application No. 62/637,129, filed on Mar. 1, 2018.

(51) Int. Cl.
| | |
|---|---|
| A61K 8/31 | (2006.01) |
| A61K 8/37 | (2006.01) |
| A61K 8/97 | (2017.01) |
| A61Q 1/10 | (2006.01) |
| A61Q 15/00 | (2006.01) |
| A61Q 19/00 | (2006.01) |
| A61K 8/92 | (2006.01) |
| A61Q 5/12 | (2006.01) |
| A61Q 19/08 | (2006.01) |
| A61Q 19/10 | (2006.01) |

(52) U.S. Cl.
CPC ............... *A61K 8/31* (2013.01); *A61K 8/37* (2013.01); *A61K 8/922* (2013.01); *A61K 8/97* (2013.01); *A61Q 1/10* (2013.01); *A61Q 5/12* (2013.01); *A61Q 15/00* (2013.01); *A61Q 19/00* (2013.01); *A61Q 19/08* (2013.01); *A61Q 19/10* (2013.01); *A61K 2800/10* (2013.01); *A61K 2800/30* (2013.01); *A61K 2800/805* (2013.01)

(58) Field of Classification Search
CPC . A61K 8/31; A61K 8/922; A61K 8/37; A61K 8/97; A61K 2800/10; A61K 2800/30; A61K 2800/805; A61Q 19/10; A61Q 5/12; A61Q 19/08; A61Q 1/10; A61Q 15/00; A61Q 19/00
See application file for complete search history.

(56) References Cited

U.S. PATENT DOCUMENTS

| | | | |
|---|---|---|---|
| 2013/0059021 A1* | 3/2013 | Grossman | A61P 17/10 424/769 |
| 2013/0085119 A1 | 4/2013 | Boskamp | |
| 2014/0356303 A1* | 12/2014 | Rocco | A61K 8/37 424/64 |
| 2016/0120778 A1* | 5/2016 | Greco | A61Q 1/14 514/512 |
| 2018/0289601 A1* | 10/2018 | Eppler | A61Q 5/00 |

FOREIGN PATENT DOCUMENTS

WO    2017059136 A1    4/2017

OTHER PUBLICATIONS

Database GNPD [Online], MINTEL; Sep. 8, 2016 (Sep. 8, 2016), anonymous: "Bio Active Conditiner", XP055584830, retrieved from www.gnpd.com; Database accession No. 4253655.
Database GNPD [Online], MINTEL; Nov. 24, 2017 (Nov. 24, 2017), anonymous: "Co Wash No Poo Cleansing Conditioner", XP055584832, retrieved from www.gnpd.com; Database accession No. 5260239.
Database GNPD [Online], MINTEL; Feb. 7, 2018 (Feb. 7, 2018), anonymous: "The Renaissance Circle", XP055584834, retrieved from www.gnpd.com; Database accession No. 5446145.
Office Action dated Jul. 27, 2020 for European Application No. 19159814.3-1112 from EPO.

* cited by examiner

*Primary Examiner* — Snigdha Maewall
(74) *Attorney, Agent, or Firm* — Cozen O'Connor

(57) ABSTRACT

Described herein is an invention that includes a spreadable conditioning composition comprising a blend of: a branched hydrocarbon and an ester having a kinematic viscosity of less than or equal to about 100 centistokes. The composition may be natural, for example, if each of the branched hydrocarbon and the ester are independently vegetable-derived. In addition, the composition may lack ingredients that are derived from a palm oil. In an embodiment, the composition is a blend of hydrogenated farnesene and an esters selected from glyceryl triheptanoate, dicapryl succinate, heptyl undecylenate, and mixtures thereof. The composition exhibits an average spreading velocity of about 4 to about 8.
Also disclosed are formulations for use in products of personal care, home/institutional care, industry, pharmaceutical and medical and veterinary care and related methods.

24 Claims, 10 Drawing Sheets
(5 of 10 Drawing Sheet(s) Filed in Color)

Glyceryl Triheptanoate

Dicapryl Succinate

Hydrogentated farnosene

FIG. 2

| Property | Sample No. | | | | | | | | |
|---|---|---|---|---|---|---|---|---|---|
| | 1 | 2 | 3 | 4 | 5 | 6 | 7 | 8 | 8 | 10 |
| Kinematic Viscosity @25 °C, cSt | 7.1 | 7.1 | 4.4 | 7.0 | 4.1 | 3.7 | 12.0 | 5.6 | 16.9 | |
| Refractive Index @25 °C | 1.4366 | 1.4331 | 1.4373 | 1.434 | 1.4358 | 1.4331 | 1.437 | | | 1.430 |
| Flash Point, °C | 122 | 130 | 132 | 136 | 122 | 122 | 188 | 170 | | |
| Specific Gravity 25°C/25°C | 0.8737 | 0.8497 | 0.8238 | 0.8655 | 0.8137 | 0.7943 | 0.917 | 0.868 | 0.964 | 0.768 |
| Pour Point °C | -60 | -60 | -39 | -69 | -36 | ND | | | | |
| Appearance | Clear, liquid | Clear, liquid | Clear, liquid | Clear, liquid | Clear, liquid | Clear, liquid | Clear, liquid | Clear, liquid | Clear, liquid | Clear, liquid |

FIG. 4

| Sample No. | Time (min) | Average Spreading Area (cm²) | Average Spreading Velocity (cm²/min) |
|---|---|---|---|
| 1 | 1 | 11.4 | 5.6 |
|   | 3 | 18.1 |   |
|   | 5 | 22.1 |   |
| 2 | 1 | 9.6 | 5.9 |
|   | 3 | 18.1 |   |
|   | 5 | 25.5 |   |
| 3 | 1 | 10.8 | 5.6 |
|   | 3 | 18.8 |   |
|   | 5 | 22.9 |   |
| 4 | 1 | 9.1 | 4.9 |
|   | 3 | 15.9 |   |
|   | 5 | 20.5 |   |
| 5 | 1 | 13.9 | 7.0 |
|   | 3 | 22.1 |   |
|   | 5 | 29.3 |   |
| 6 | 1 | 14.5 | 7.1 |
|   | 3 | 24.7 |   |
|   | 5 | 28.3 |   |
| 7 | 1 | 4.50 | 2.6 |
|   | 3 | 8.6 |   |
|   | 5 | 11.4 |   |
| 8 | 1 | 7.1 | 3.4 |
|   | 3 | 11.4 |   |
|   | 5 | 13.2 |   |
| 9 | 1 | 8.6 | 4.3 |
|   | 3 | 14.5 |   |
|   | 5 | 17.4 |   |
| 10 | 1 | 15.2 | 7.7 |
|   | 3 | 26.4 |   |
|   | 5 | 31.2 |   |

IMMEDIATELY AFTER APPLICATION

FORMULA A　　　FORMULA B　　　SECRET AUSTRALIA　　　DOVE INVISIBLE

AFTER ONE HALF HOUR

FORMULA A      FORMULA B      SECRET AUSTRALIA      DOVE INVISIBLE

AFTER ONE HOUR

FORMULA A      FORMULA B      SECRET AUSTRALIA      DOVE INVISIBLE

EA　　　　　　　　　　　EB

EA                    EB

NATURAL HYDROCARBON/ESTER COMPOSITIONS WITH IMPROVED SENSORY PROPERTIES, FORMULATIONS AND RELATED METHODS

CROSS REFERENCE TO RELATED APPLICATION

This application claims the benefit under 35 U.S.C. § 119(e) of U.S. Provisional Patent Application No. 62/637,129, filed on Mar. 1, 2018, entitled "Natural Hydrocarbon/Ester Compositions With Improved Sensory Properties, Formulations and Related Methods" the entire disclosure of which is incorporated herein by reference.

BACKGROUND OF THE INVENTION

Personal care and cosmetic products appeal to consumers not only due to beauty and hygiene concerns, but also as a means of social integration and well-being. However, amongst all attributes of such products, consumers rely primarily on sensorial aspects to decide if they will purchase the same product again. Most personal care and cosmetic carriers are a composition of both water and oil phases stabilized according to the principles of emulsion technology, but full oil-based, alcohol or other solvent based, or aqueous solution-based formulations are also alternatives.

When water or any other volatile materials are present in a personal care product that is applied to, for example, skin, they evaporate after application due to regular body temperature. The non-volatile components, such as emollient oils, are left behind. Emollient oils condition the skin, hair or nails. By conditioning, it is meant refatting, lubricating, softening and smoothing, and/or reducing the appearance of fine lines and wrinkles.

Although many emollient oils are effective in conditioning skin, many may leave an unpleasant after-feel, an unctuous feeling, or a shininess that is not desired. What is often desired is effective conditioning without the aforementioned negative attributes. What is highly desired by consumers is effective conditioning in a platform that results in an after-feel described as "light."

One aspect that strongly affects the achievement of "lightness" is, in addition to the property of the oils themselves, the thickness of the residual oil layer that remains on the treated surface. The property of "spreadability" refers to the ability of a liquid substance to spread over the surface of a certain substrate, that is, the rate at which the liquid moves from the application area to the surrounding area, and the distance from the application area. In the case of, for example, skin applications, the spreadability of a material affects its residual thickness, which in turn relates to the user's perception of "lightness". A higher spreading material leads to a larger spreading area, and thus a thinner film remains.

Spreadability is also related to viscosity, to the affinity of the liquid for the substrate (adhesiveness) and the affinity of the liquid for itself (cohesiveness.) For this reason, a low viscosity liquid may spread more slowly than a higher viscosity liquid. As an example, water, a highly polar and very low viscosity liquid, does not spread at all on the non-polar surface material Teflon® (polytetrafluoroethylene). Water has high affinity for itself, and no affinity for Teflon®.

Fatty ester oils ("esters") are used as emollients and conditioning agents, and are included in compositions meant to be used on keratinized surfaces, such as the skin, hair and nails. The ester linkage in ester materials is polar. Keratinized surfaces such as skin, hair and nails are also polar. Because of this, esters are adhesive to these substrates.

Esters adhere through polar-polar interactions and for that reason provide conditioning benefits, especially on the skin. This polar-polar interaction also makes the ester molecules adhere to themselves which makes them cohesive, and lowers their spreadability.

Conventional personal care products relied upon petrochemically derived esters delivered to these skin or "silicone fluids"/hair/nails in volatile carriers or solvents such as silicone oils or fluids. Volatile silicone oils, such as the cyclomethicones and lower molecular weight dimethicones, are essentially non-polar, so they are poorly adhesive and poorly cohesive. They possess a low contact angle to the hair and skin, which relates to faster spreadability, and are volatile—evaporating from surfaces at room temperature. Because of their volatility, silicone oils do not function as emollients or conditioning agents because they do not remain on the substrate. They are, however, useful for delivering non-volatile emollients, actives and other components such as higher viscosity esters to the substrate in applications such as antiperspirants. When blended with other ingredients such as emollients and polymers, silicone oils increase the overall spreadability on the material, resulting in a thinner residual layer remaining on the skin surface giving a desired, lighter skin feel. However, the silicone oils are also derived from petrochemicals.

The trend to move away from use of petrochemical-derived ingredients in personal and home care remains strong. Products derived from renewable resources such as vegetable/plant matter can be presented to consumers as "natural" in contrast to pertrochemically derived materials. In addition, many manufacturers prefer to avoid ingredients derived from "palm oil", e.g., from plants of the genera *Elaeis* or *Attalea*, such as the African oil palm *Elaeis oleifera, Elaeis guineessis* and/or the *maripa* palm *Attalea maripa* in view of concerns related to deforestation, microclimate change, and indigenous specie's habitat disruption.

To date, some 100% vegetable-derived low viscosity esters have been developed and commercialized such as LexFeel Natural (heptyl undecylenate, INOLEX, Inc., USA), SustOleo DCS (diisooctyl succinate, INOLEX, Inc. USA) and SustOleo MCT (triheptanoin, INOLEX Inc., USA.) Furthermore, each of these products is not derived from palm oil.

Hydrocarbon fluids are also known for use as carrier fluids and solvents. Many are volatile, and like volatile silicones, they are non-polar and also give rise to low contact angle on the substrate which relates to faster spreadability. For example, the Parafol (Sasol, Germany) series of linear hydrocarbons are derived from both coconut and palm sources. Another example is Neossance Hemisqualane (Amyris, USA) which is hydrogenated farnesene, a branched hydrocarbon substance containing 15 carbon atoms overall.

The parent material, farnesene is derived from the fermentation of sugar cane, for example, as is described in WO2017059136 A1, the contents of which is incorporated herein by reference.

Use of ester oils blended with hydrocarbons have been disclosed. For example, WO2004103308 A2 describes mixtures of esters derived from neopentyl glycol with isododecane to replicate the feel of cycloinethicone fluids; however, these mixtures are derived from materials of petrochemical origin, and therefore cannot be described as natural.

WO2010115973A1 discloses mixtures of linear hydrocarbons derived from coconut with non-volatile oils that purportedly mimic the feel of silicones. Branching in the alkane structure provides a lighter feeling because they are not able to pack together as tightly as linear alkanes. There is a need in the industry for efficient methods to improve the spreadability of a non-volatile liquid emollient esters, and thus improve the feel. Surprisingly, while studying emollient spreadability on the skin and on skin-like substrates, the present inventors have found a method to improve esters spreadability, which results in improved sensory characteristics.

BRIEF SUMMARY OF THE INVENTION

Described herein is an invention that includes a spreadable conditioning composition comprising a blend of: a branched hydrocarbon and an ester having a kinematic viscosity of less than or equal to about 100 centistokes. The composition may be natural, for example, if each of the branched hydrocarbon and the ester are independently vegetable-derived. In addition, the composition may lack ingredients that are derived from a palm oil. In an embodiment, the composition is a blend of hydrogenated farnesene and an esters selected from glyceryl triheptanoate, dicapryl succinate, heptyl undecylenate, and mixtures thereof. The composition exhibits an average spreading velocity of about 4 to about 8.

Also disclosed are formulations for use in products of personal care, home/institutional care, industry, pharmaceutical and medical and veterinary care.

The invention includes methods of preparing a surface conditioning formulation comprising mixing the composition described above with an additional ingredient, such as, for example, a surfactant, a colorant, a detersive agent, a mechanical sunscreen, a fragrance, a chealtor, an antioxidant, a UV absorbing compound, a particulate and a solvent or of preparing a natural composition having an average spreading velocity of about 4 to about 8 comprising blending a natural branched hydrocarbon with an natural ester having a kinematic viscosity of less than or equal to about 100 centistokes.

Methods of use of the composition include, for example, methods of increasing the spreadability of a conditioning agent that include combining the conditioning agent with a branched hydrocarbon, wherein the conditioning agent is an ester having a kinematic viscosity of less than or equal to about 100 centistokes; methods of delivering a material to a surface by applying a formulation of the invention to the surface whereon the formulation contains the composition of the invention and an additional ingredient, such as, for example, a UV absorbing agent, a biologic, a patinator, an antimicrobial agent, an antioxidant, a mica, glitter, a pigment, an anti-rust agents, an anti-tarnish agent, a whitener, and a self-tanner.

BRIEF DESCRIPTION OF THE SEVERAL VIEWS OF THE DRAWINGS

At least one Figure that is a color photograph is included herein. Copies of this patent or patent application publication with color drawings will be provided by the Office upon request and payment of the necessary fee.

The foregoing summary as well as the following detailed description of embodiments of the invention, may be better understood when read in conjunction with the appended drawings. For the purpose of illustrating the invention there is shown in the drawings embodiments which may be preferred. It should be understood, however, that the invention is not limited to the precise arrangements and instrumentalities shown. In the drawings:

FIG. 2 is a chart showing the values for various physical and chemical properties of the inventive and comparison compositions;

FIG. 4 is a chart showing the average spread velocity data gathered for each sample;

DETAILED DESCRIPTION OF THE INVENTION

Figure 1:
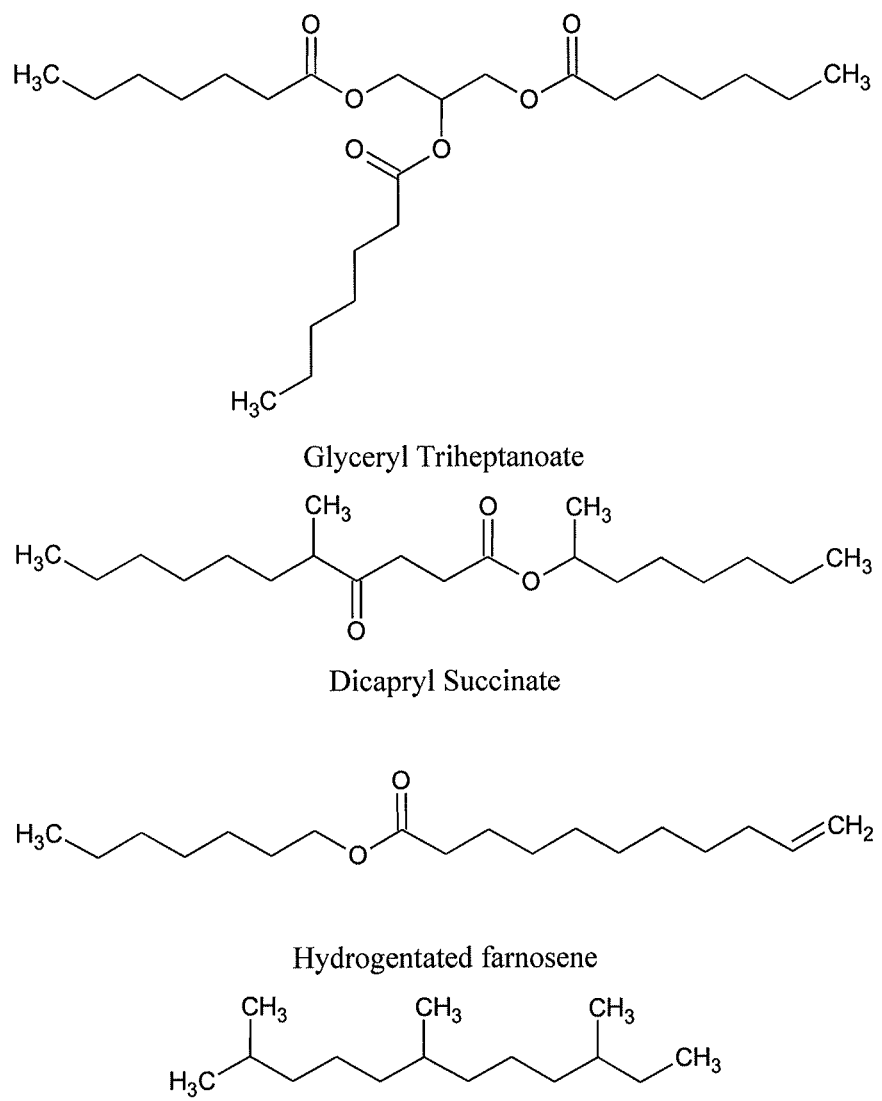
FIG. 1 shows the chemical structures of exemplary components of the composition of the invention.

The invention as described herein include a conditioning or emollient composition providing multifaceted advantages, in addition to its conditioning properties. For example, when applied to the skin or other keratinized surfaces, it has a high average spread velocity which results in a composition that conditions the surface while providing to the user a "light", not greasy skinfeel. It can be prepared to be 100% natural, as all its components may be vegetable derived. However, use of palm oil derived ingredients can also be avoided. Within the scope of the invention are, without limitation, the composition itself, methods of using and/or making the composition, methods of improving the average spread velocity of a emollient ester, end products, such as personal care, pharmaceutical, or industrial, institutional and/or home care products or formulations that contain the composition, and method of conditioning surface, such as a keratinized surfaces, the surface of a textile or fiber and the like, by applying the compositions of the invention.

As used herein, "conditioning" means accomplishing any one or more of refatting, lubricating, smoothing, softening, patinating, and/or, with respect to living skin, reducing the appearance of fine lines and wrinkles. A "conditioning agent", therefore, is a material that is chemically capable of carrying out any one or more of fatting, lubricating, smoothing, softening, patinating, and/or, with respect to living skin, reducing the appearance of fine lines and wrinkles.

If desired, the conditioning composition of the invention can be prepared to be 100% natural, that is, to have an absence of any ingredients that are derived from petrochemicals. In an embodiment, all components of the composition are obtained from botanical and plant (i.e., "vegetable") sources. Such sources may include, without limitation, plants of the genera *Pruna*, plants of the family Arecaceae, coconut, palm, almond, castor, corn (maize), cottonseed, flax seed, hempseed, nut, olive, peanut, safflower, sesame, soybean, sunflower, jojoba, and combinations thereof.

In the practice of the invention, each of the ester(s), branched hydrocarbons, and/or any additional components may be vegetable-derived (i.e., "natural"). If all components are vegetable-derived, one may refer to the entire composition or formulation as "natural".

The invention includes an ester or mixture of esters which may serve as the emollient or conditioning agent. Any ester(s) may be used. However, it may be preferred that the selected ester has a kinematic viscosity of less than or equal to about 100 centistokes, alternatively, less than or equal to about 75 centistokes, less than or equal to about 50 centistokes, or less than or equal to about 25 centistokes, when viscosity is measured by the protocol set forth in ASTM method D445, American Society for Testing and Materials, Conshohocken, N.Y. (see, Appendix A).

In an embodiment, the ester selected has about 1 to about 15 ester linkages, or about 2, about 3, about 4, about 5, about 6, or about 7 ester linkages. The linkages may be on the main chain of the ester molecule or on the substituents; however, it may be preferred that at least one to 4 of the linkages is on the main chain of the ester molecule.

Esters of any size/molecular weight may be used; however, in an embodiment, the ester has about 15 to 30 total carbons.

In an embodiment, the ester is selected from glyceryl triesters of medium chain carboxylic acids, diesters of medium chain diacids with medium chain linear or branched alcohols, monoesters of medium chain carboxylic acids with medium chain alcohols and mixtures thereof. (In all instances, "medium chain" is a hydrocarbon chain of about 6 to about 1 carbon atom(s)). It may be preferred that the ester is, for example, one or more of glyceryl triheptanoate, dicapryl succinate, heptyl undecylenate, and mixtures thereof. The chemical structures of these exemplary esters are shown in FIG. 1. These materials can be purchased from, for example, INOLEX, Inc, as SustOleo DCS, SustOleo MCT and LexFeel Natural.

The invention includes a hydrocarbon, preferably a branched hydrocarbon. With reference to IUPAC naming conventions, in an embodiment, the branched hydrocarbon includes a main hydrocarbon chain which bears at least one substituent chain (i.e., "branch"). The branched hydrocarbon may contain any number of carbon atoms in total (i.e., main chain plus the substituent chain(s) or branches) and/or in the main chain alone, if no branching is present.

In an embodiment, it may be preferred that the branched hydrocarbon contains about 10 to about 70, about 20 to about 50 or about 30 to about 40 carbon atoms in total. In a version of the inventive composition, the branched hydrocarbon contains about 9, about 10, about 11, about 12, about 13, about 14, and about 15, about 16, about 17, about 18, or about 19 carbon atoms in total.

With respect to the main hydrocarbon chain, in some embodiments, it may be desirable for the main hydrocarbon chain to have 5 to 50 or has 10 to 30 carbon atoms.

In an embodiment, it may be preferred that the substituent chain(s) are independently methyl groups ($-CH_2$); alternatively, the substituent chains independently may have any number of carbon atoms, or be ethyl, propyl, butyl, pentyl hexyl, and/or heptyl. All of the substituent chain(s) on a given main hydrocarbon chain may be the same or different.

As noted above, the hydrocarbon is branched in that it has a main hydrocarbon chain that bears at least one substituent chain or "branch". In an embodiment, the branched hydrocarbon has at least 3 branches, or about 2 to about 10, about 4 to about 5, branches that are on or extend from the main hydrocarbon chain.

In any embodiment that may be preferred, the branched hydrocarbon has a total carbon atom content represented by "X", and a main hydrocarbon chain having a carbon atom content represented by "Y". "X" is an integer of 13 to 50 and "Y" is 10 to 30 carbon atoms; alternatively, "X" is 15 carbon atoms and "Y" is 12 carbon atoms. In such instances, the carbon atoms not in the main hydrocarbon chain (that is, the difference between X and Y (e.g., X minus Y) serve to form one or more substituent chains from the main hydrocarbon chain.

In an embodiment, the branched hydrocarbon is hydrogenated farnesene, the structure of which is shown in FIG. 1.

Regardless of specific structure, it may be preferred that the selected branched hydrocarbon(s) has a kinematic viscosity of less than or equal to about 100 centistokes, alternatively, less than or equal to about 80 centistokes, less than or equal to about 60 centistokes, or less than or equal to about 30 centistokes, when viscosity is measured by the protocol set forth in ASTM method D445, American Society for Testing and Materials, Conshohocken, N.Y. (see, Appendix A).

The composition is prepared by mixing the fluids in a suitable vessel to homogeneity. The amount of each of the ester and branched hydrocarbon components will vary depending on several factors, such as specific components selected, inclusion of other ingredients, end product to be formulated, end properties desired, etc. In general, it may be preferred that the branched hydrocarbon and the ester are present in a relative weight ratio (wt % hydrocarbon:wt % ester) that is one of: about 2:about 3, about 1:about 2.5, about 1:about 1, or about 2.5:about 1.

The composition may be prepared in advance, for example, as a concentrate or an admixture, an applied to the surface as-is. Or, it may subsequently be incorporated into a second prepared formulation to provide an end product. Attentively, the individual components may be added to a prepared formulation to form an end product. End products might be, for example, personal care products, home/institutional care products, industrial products, and/or pharmaceutical or veterinary products.

In embodiments where no other ingredients are present, it may be preferred that the branched hydrocarbon is present in the composition in an amount of about 30% to about 80% by weight of the total composition, about 40% to about 70% by weight of the total composition, or about 50% to about 60% by weight of the total composition.

Correspondingly therefore, it may be preferred that the ester is present in the composition in an amount of about 20% to about 70% by weight of the total composition, about 30% to about 50% by weight of the total composition, or 35% to about 45% by weight of the total composition.

Other ingredients may be included in the composition of the invention either to aid in the ease of manufacture, shipping and/or storage, or to provide the end user/consumer with added benefits or experiences. Examples are preservatives, colorants, fragrances, particulates, lipids, proteins, sensates and chelators. Moreover, by virtue of the composition's high average spread velocity, it provides an adherent thin film that is suitable for delivery of various additional agents to the surface to which it is applied. Without limitation, such agents may include mechanical sunscreens, UV light absorbers, pharmaceutical agents including biologics, patinators, antimicrobial agents, antioxidants, mica, glitter, pigments, anti-rust agents, anti-tarnish agents, a whitener, an optical brightener, a bluing agent, and/or self-tanners.

The composition of the invention may be incorporated into personal care, pharmaceutical, home/institutional care and industrial products for application to various surfaces, such as for example, hard surfaces, metals, wood, stone, tanned hides, furs and hairs, textiles, natural and synthetic fibers, and keratinized surfaces, such as hair, skin, nails/ claws and hooves. It may contain substantially only the hydrocarbon and the ester, or other ingredients may be included.

Such products may also include other ingredients as is routine for the relevant product category, such as, for example, surfactants, fragrance, colorants, stabilizers, builders, ammonia, detersive agents, particulates, additional moisturizers or conditioners, glycerin, solvents, water, humectants, smectite and/or other clays, limonene, etc., as well as the additives listed above.

The composition of the invention can be used in method of increasing the spreadability of a conditioning agent, where the conditioning agent is a an ester having a kinematic viscosity of less than or equal to about 100 centistokes and/or is one or more of glyceryl triesters of medium chain carboxylic acids, diesters of medium chain diacids with medium chain linear or branched alcohols, monoesters of medium chain carboxylic acids with medium chain alcohols and mixtures thereof.

All permutations of the elements described above, including the presence or absence of an elements, are contemplated in the embodiments of the compositions, formulations, and/or the methods of the invention.

EXAMPLES

Example 1

Preparation and Analysis of Compositions of the Invention

Ten compositions were prepared contain the ingredients shown below in Table 1.

TABLE 1

| Sample No. | Ingredients | Amount (by weight percent of the total sample composition) |
| --- | --- | --- |
| 1 | Glyceryl Triheptanate | 60.0 |
|   | Hydrogenated Farnesene | 40.0 |
| 2 | Dicapryl succinate | 60.0 |
|   | Hydrogenated Farnesene | 40.0 |
| 3 | Heptyl undecylenate | 60.0 |
|   | Hydrogentated farnesene | 40.0 |
| 4 | Dicapryl succinate | 70.0 |
|   | Hydrogenated Farnesene | 30.0 |
| 5 | Heptyl undecylenate | 50.0 |
|   | Hydrogentated farnesene | 50.0 |
| 6 | Heptyl undecylenate | 30.0 |
|   | Hydrogentated farnesene | 70.0 |
| 7 | Triheptanoin | 100.0 |
| 8 | Dicapryl succinate | 100.0 |
| 9 | Heptyl undecylenate | 100.0 |
| 10 | Hydrogentated farnosene | 100.0 |

All of the components are liquids at room temperature. The samples were each prepared by adding to a suitable vessel and agitating to homogeneity.

Each of the samples was evaluated for the following properties using the analytical methodologies shown in Table 2.

TABLE 2

| Property | Units | Analytical Method |
| --- | --- | --- |
| Kinematic Viscosity | cSt | ASTM D445 |
| Refractive Index | — | ASTM D1218 |

TABLE 2-continued

| Property | Units | Analytical Method |
| --- | --- | --- |
| Flash Point | °C. | ASTM D92 |
| Specific Gravity | — | ASTM D891 |
| Pour Point | °C. | ASTM D97 |
| Appearance | — | Visual Observation |

The contents of each ASTM are incorporated herein by reference.

The results of the evaluation are shown in FIG. 2.

Example 2

Evaluation of Average Spread Velocity as a Measure of Spreadability

The spread velocity of each of the sample compositions 1-10 was evaluated using the following general procedure. An artificial skin substrate was used to determine average spreading velocity. Spreading is the rate at which the spreading area increases. Spreading always is fastest the moment the liquid touches the substrate, and then slows asymptotically to zero with time.

Figure 3:
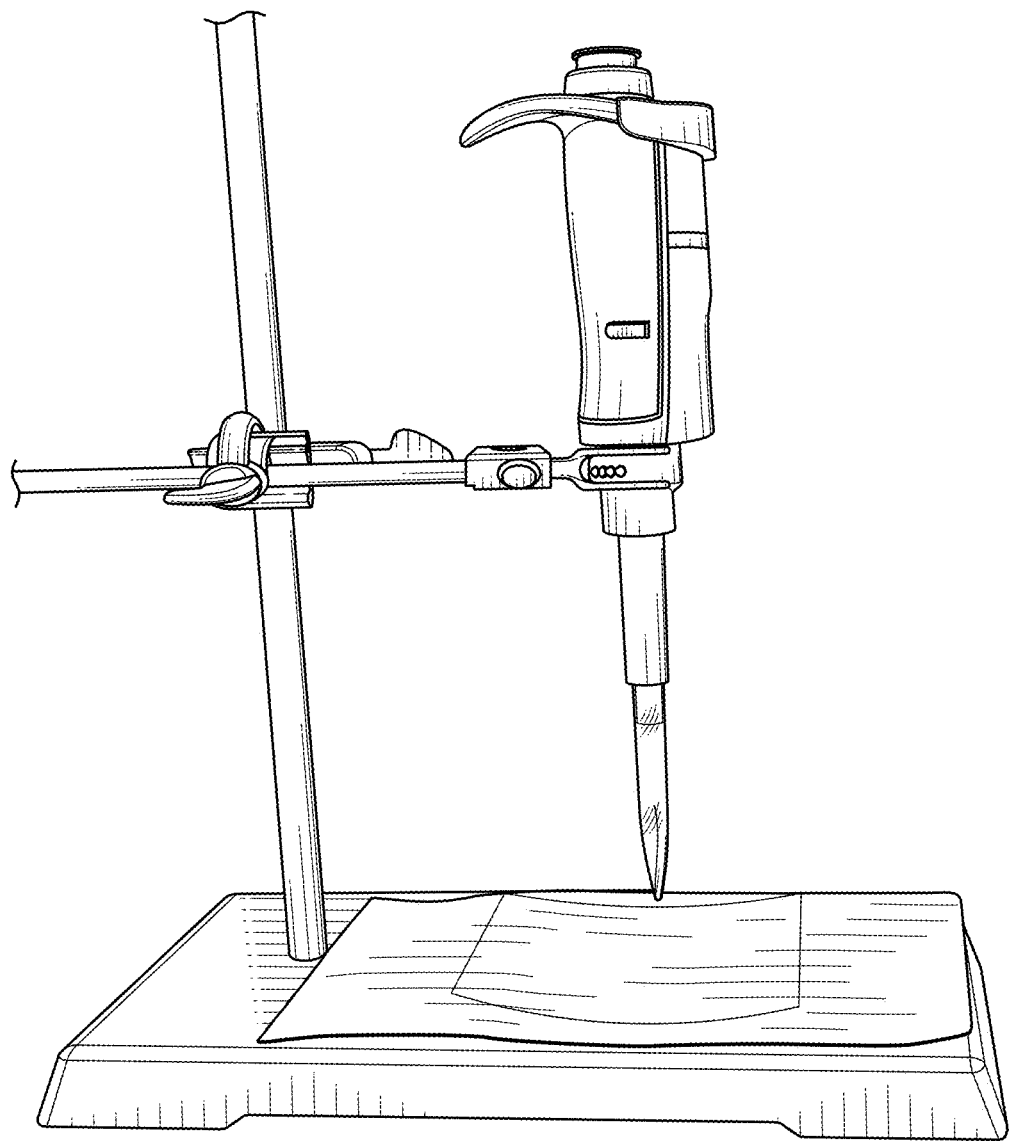
FIG. 3 is a photograph of an exemplary experimental apparatus used to evaluate average spread velocity.

To determine these values, a 3×3 inch square piece of VITRO-SKIN® (IMS, Inc., Portland, Me., USA) membrane was previously hydrated in a humidity chamber set at room temperature (23° C.) and 60% humidity, for 16 hours. A micropipette was filled with test material and placed exactly 1-inch above the artificial membrane using a ring stand. The experimental set-up is shown in FIG. 3.

A drop of sample composition (50 µL) was delivered to a central location onto the 3×3 inch square of VITRO-SKIN®. Spreading proceeds outward from the contact point and creates a circular spot. Since the wetted circular area of the VITRO-SKIN® can be seen, the diameter can be measured. This spreading diameter was measured after 1, 3 and 5 minutes of contact. The spreading area is determined taking the diameter of the spot in centimeters, halving to get the radius, squaring the radius, then multiplying by $\pi$. The resulting data will give an area at the 1, 3, and 5 minute time point. By subtracting the area at each time point from the area at the previous time point, the incremental additional area covered can be calculated. Thus the average spreading velocity can be determined by dividing the area covered by the time interval for each interval, then dividing by the total number of time intervals. Thus the equation for determining average spreading velocity for three time intervals per the experiments is as follows:

$SA_{t1} = [(D1\ cm/2)^2 \pi$   Units are $cm^2 \cdot t1 = 1\ min. - 0\ min. = 1\ min.$
$SA_{t2} = [(D2\ cm/2)^2 \pi$   Units are $cm^2 \cdot t2 = 3\ min. - 1\ min. = 2\ min.$
$SA_{t3} = [(D3\ cm/2)^2 \pi$   Units are $cm^2 \cdot t3 = 5\ min. - 3\ min. = 2\ min.$ Wherein:
D1=diameter of circle after 1 minute
D2=diameter of circle after 3 minutes
D3=diameter of circle after 5 minutes
SAt1=area of circle after 1 minute
SAt2—area of circle after 3 minutes
SAt3=area of circle after 5 minutes
Therefore, the average spreading velocity=

$$[(SA1-0)cm^2/1\ min. + (SA2-SA1)cm^2/2\ min + (SA3-SA2)cm^2/2]/3$$

For each sample number, the average spread velocity was determined. The results are shown in FIG. 4. The results are the average of three determinations.

Example 3

Sensory Analysis by Panelists

Sensory analysis of personal care and cosmetic products relies on panelists' perception to assess and compare attributes of each product during all steps of human use. In this example, panelists focused on describing their perception after picking up, rubbing out and feeling the product on the skin after application ("after-feel").

During the pick up step, panelists evaluated "stickiness", which is the intensity of finger adherence to the skin, and was tested using the tips of index and thumb fingers.

In the rub out step, panelists assessed "spreadability", which is the ease of distributing the product over the skin, and was tested by rubbing the product on the forearm with the opposite hand.

Finally, in after-feel step, panelists were instructed to consider slipperiness, residue and gloss. "Slipperiness" is the ease with which one can move two fingers over the forearm skin after the product was rubbed out. "Residue" is the perception of the amount of product left on the skin after the product was rubbed out, as perceived on the fingertips. "Gloss" is the amount or degree of light reflected off the skin, as seen under the same light settings.

Prior to testing of the sample compositions, all panelists were previously trained on the meaning of each technical terminology and on how to judge each aspect of this sensory analysis (pick up, rub out and after-feel). Before evaluating test-formulations, the panel was calibrated by trying standard reference samples for low and high levels of each one of the five parameters (stickiness, spreadability, slipperiness, residue and gloss).

Even though panelists perceived different intensities for each reference, they all agreed on which samples represented the lower and the higher level of each parameter. Procedures used in this sensory panel were based on the recommendations of the American Society for Testing and Materials (ASTM E1958, the contents of which are incorporated here by reference.)

Example 4

Formulation of An Antiperspirant Stick Containing the Composition of the Invention Whitening of the skin or clothing is undesired in antiperspirant sticks that contain solid antiperspirant actives such as aluminum salts. Common aluminum salts used in antiperspirant applications are Aluminum Chlorohydrate (ACH), Activated Aluminum Chlorohydrate (AACH), Conventional Aluminum Zirconium Actives (ZAG Actives), and Activated Aluminum Zirconium Actives (AZAG). A typical antiperspirant stick may comprise a waxy substance, a film-former, a fragrance, and a volatile carrier fluid. The example below shows how the composition of the invention can reduce whitening.

Exemplary anti-perspirant sticks were prepared according to the following composition. Cyclomethicone, a common silicone material was the comparative prior-art fluid.

TABLE 2

| Phase | Trade Name | Ingredient INCI Name | A wt. % | B wt. % |
|---|---|---|---|---|
| A | SustOleo BG[1] | *Brassica* Glycerides | 25.0 | 25.0 |
|   | LexFeel 700[1] | Polyester-4 | 5.0 | 5.0 |
| B | GK9330 | Hydrogenated Farnasane (and) Heptyl Undecylenate | 25.0 | 0.0 |
|   | Cyclo-2244[2] | Cyclotetrasiloxane | 20.0 | 45.0 |
|   | Reach AZP-908[3] | Aluminum/Zirconium Tetrachlorohydrex-GLY | 24.0 | 24.0 |
| C | Perfume Essence N26280[4] | Fragrance | 1.0 | 1.0 |
| Total |  |  | 100.0 | 100.0 |

[1]INOLEX, Incorporated;
[2]Clearco Products Co., Inc.;
[3]Summit Reheis;
[4]Carruba The formulation was made by blending the ingredients of Phase A in a beaker. In a separate beaker, the components of Phase B were blended together using a Speed Mixer. Phase B is was then added to Phase A, and stirred with a magnetic stirrer, then heated to 80° C. and held for 10 to 30 minutes. The mixture was allowed to cool to 70°, and Phase C was then added. The mixture was allowed to cool to 65° and poured into canisters, then allowed to cool to room temperature. What resulted in each case was a solid stick.

Figure 5:
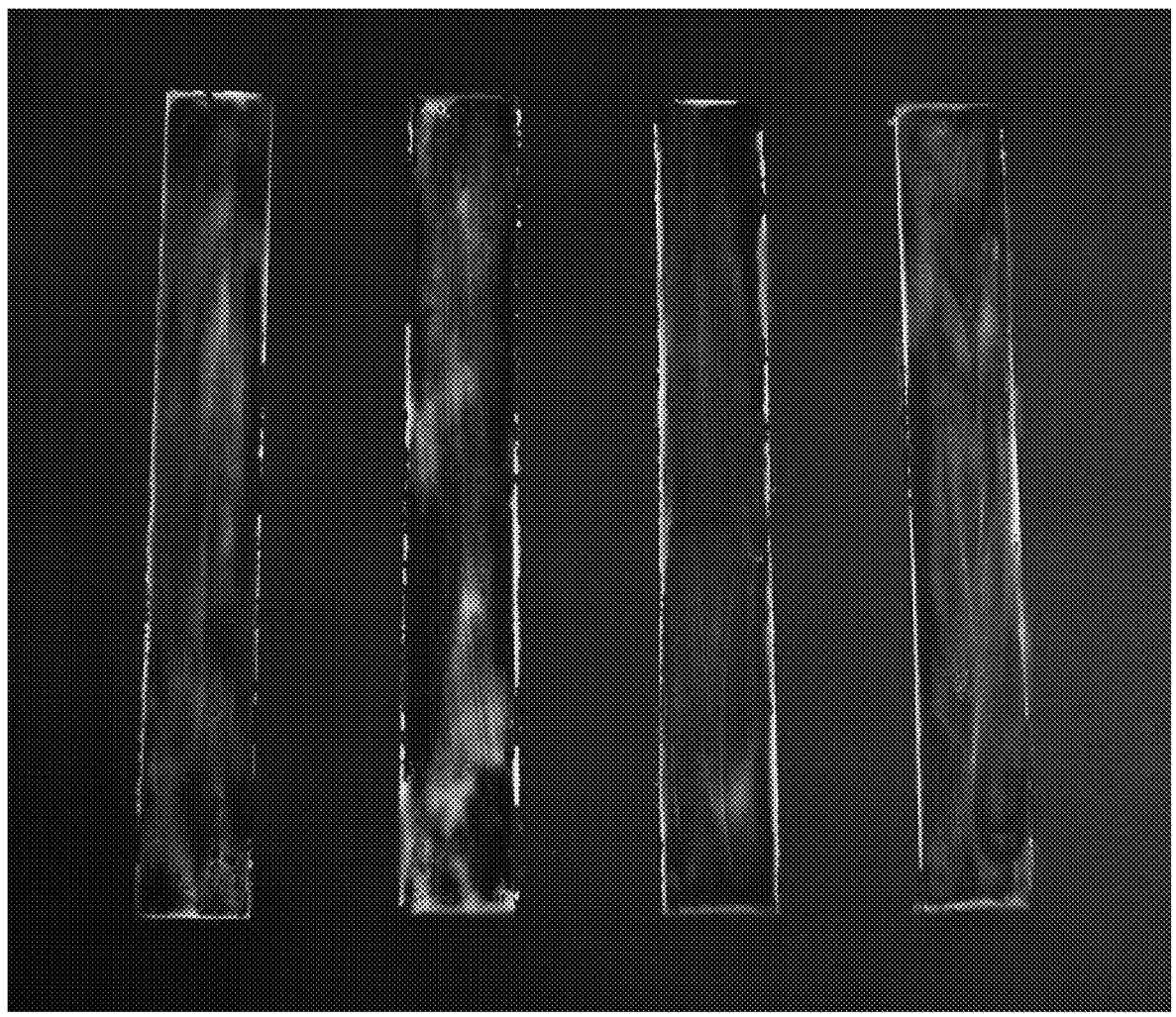
FIGS. 5, 6, and 7 are photographs demonstrating the reduction in whitening for an antiperspirant composition made in accordance with the invention.
Figure 6:
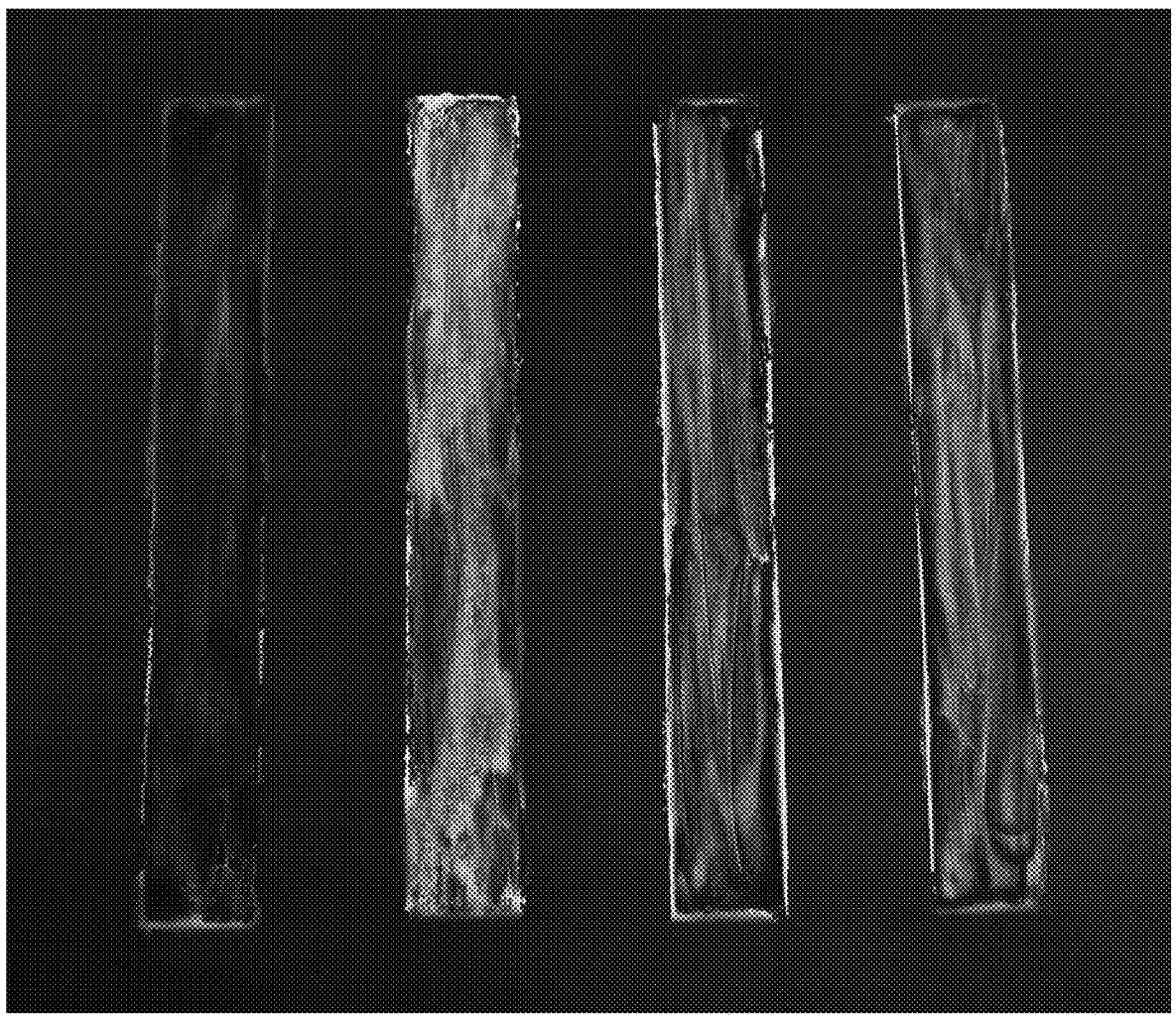
Figure 7:
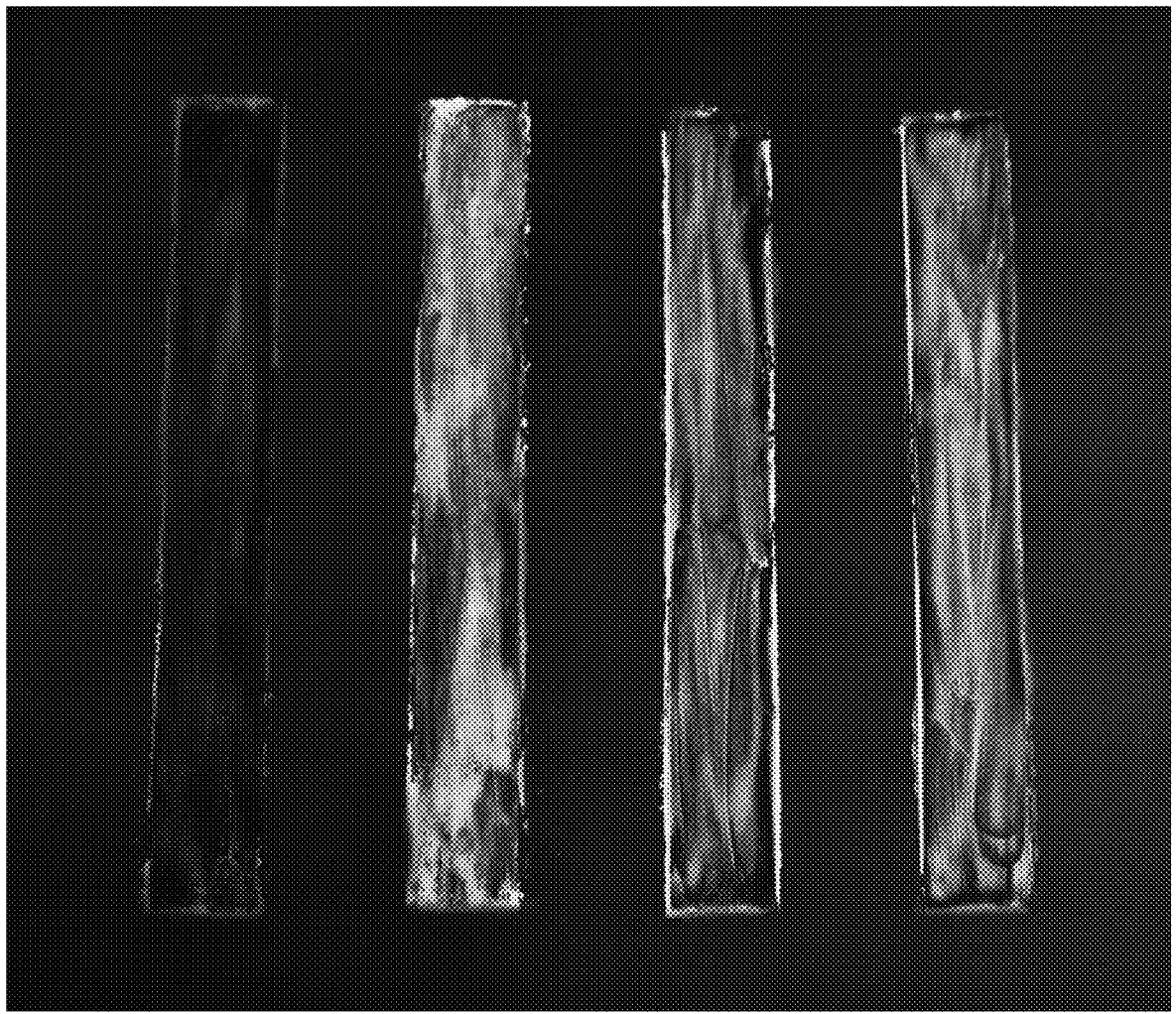

To illustrate the reduction in whitening, the sticks were rubbed on to black paper. Photos were taken at time zero (initially), after about one half hour, and after one hour. FIGS. 5, 6, and 7 show formula A which contains the inventive composition, formula B which is the control composition, and two commercial antiperspirants, "Secret Australia Eucalyptus Blossoms" made by Procter & Gamble, Cincinnati Ohio, USA and Dove Powder Invisible Solid, made by Unilever (Port Sunlight, England) at the three timepoints.

The photos of FIGS. 5, 6, and 7 show a dramatic reduction in whiting from the inclusion of the inventive composition of Sample No. 6 of Example 1.

Example 5

Formulation of An Eyeshadow Containing the Composition of the Invention

Desirable attributes in color cosmetics such as eyeshadow pots include ease of pick-up, improved color pay-off, the feeling of richness, and a moisturizing feeling in the after-feel. By color pay-off it is meant the amount depth and vibrance of the color observed given the application of equal amounts of product. That is to say, if the same amount of product A is applied to the skin as product B, if product B shows a higher depth of color, it is considered to be better. Also, a more pleasant, silky and smooth after-feel is a desired attribute.

The formulations below were prepared as examples of prior art and inventive eye shadows for comparison. Cyclomethicone, a common silicone material was the comparative prior-art fluid. Formula EA includes the inventive composition, while EB does not.

TABLE 3

| Trade Name | Ingredient INCI Name | EA wt. % | EB wt. % |
|---|---|---|---|
| LexFeel 700[1] | Polyester-4 | | |
| GK9330 | Hydrogenated Farnasane (and) Heptyl Undecylenate | 24.00 | 24.00 |
| Cyclo-2244[2] | Cyclotetrasiloxane | 35.25 | 0.00 |
| Orgasol 2002 D Nat COS[3] | Nylon-12 | 0.00 | 35.25 |
| Silica[4] | Silica | 2.35 | 2.35 |
| Colorona Dark Blue[5] | Mica (and) Titanium Dioxide (and) Ferric Ferrocyanide | 5.90 | 5.90 |
| Diamond Cluster[6] | Mica (and) Titanium Dioxide | 10.85 | 10.85 |
| SustOleo TB[1] | Hydrogenated Rapeseed Oil | 7.00 | 7.00 |
| Ozokerite | — | 5.90 | 5.90 |

[1]INOLEX, Incorporated;
[2]Clearco Products Co., Inc.

To prepare the formulations, the components of Phase A were combined in a beaker using a high speed mixer at a stirring rate of 3500 rpm. The components of Phase B were then added, and the mixture was heated to 80° C. and stirred using a magnetic stirrer. When the mixture became smooth and homogeneous, the mixture was allowed to cool and then was poured off into containers, and allowed to cool to room temperature.

Figure 8:
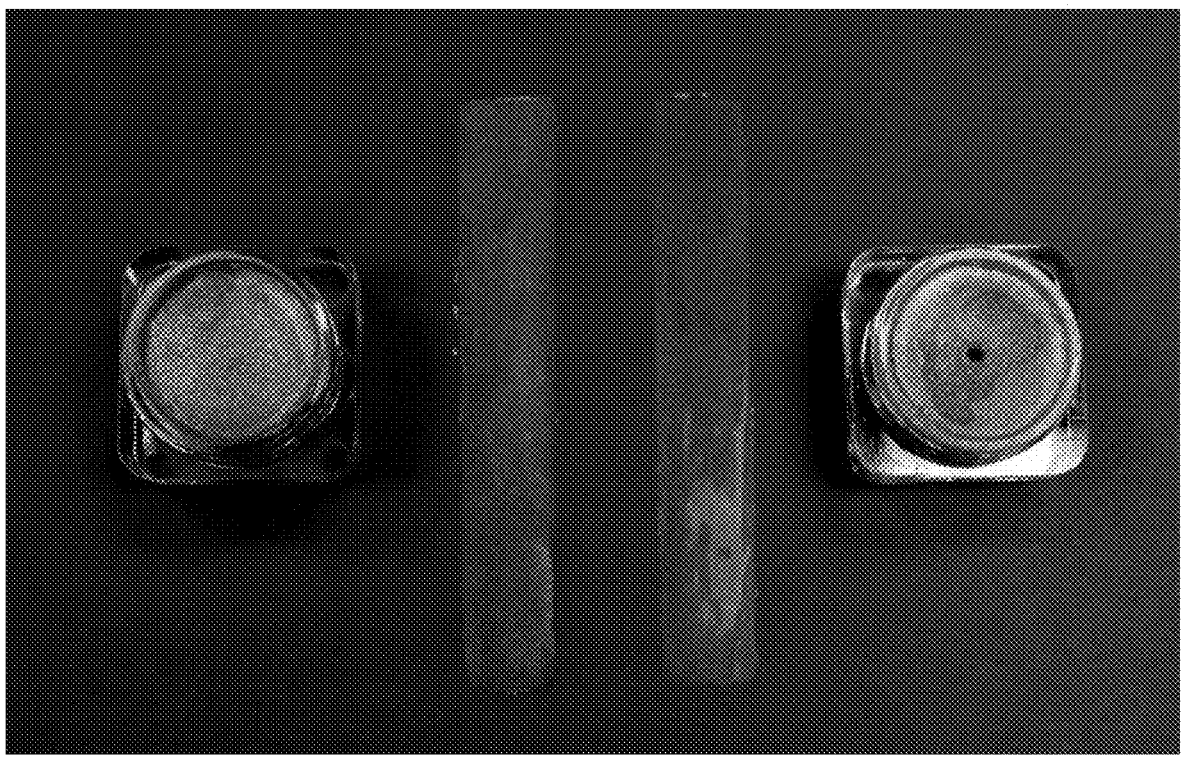
FIGS. 8 and 9 are photographs illustrating the difference in color pay off among the various samples.
Figure 9:

To illustrate color pay-off, equal amounts of each formulation were rubbed on to black paper. FIGS. 8 and 9 show photos showing the improvement in color pay-off on the black paper and on human skin.

Example 6

Preparation of a Cationic Lotion

To illustrate the improved sensory properties that can be obtained using the inventive fluid relative to the very popular prior art fluid, cyclopentasiloxane, the following cationic lotions were prepared.

TABLE 4

| Phase | Trade Name | Ingredient INCI Name | A wt. % | B wt. % |
|---|---|---|---|---|
| A | — | Deionized Water | 1.15 | 1.15 |
| | — | Glycerine | 3.00 | |
| | — | L-Aspartic Acid[3] | 0.75 | 0.75 |
| | — | Preservative | | |

TABLE 4-continued

| Phase | Trade Name | Ingredient INCI Name | A wt. % | B wt. % |
|---|---|---|---|---|
| B | SustOleo 1822[1] | Brassicamidopropyl Dimethylamine | 2.00 | 2.00 |
| | SustOleo GMS[1] | Glyceryl Stearate | 2.00 | 2.00 |
| | — | Cetyl Alcohol | 3.00 | 3.00 |
| | Cyclo-2245[2] | Cyclopentasiloxane | — | 5.00 |
| | SustOleo BA[1] | Brassica Aclohol[1] | | |
| | SustOleo MCT1 | Triheptanoin[1] | 8.00 | 8.00 |
| C | Perfume Essence N262754 | Fragrance | 0.10 | 0.10 |
| | | Total | 100.00 | 100.00 |

[1]INOLEX Inc.;
[2]Clearco Products Co., Inc.;
[3]Ajinomoto
[4]Carruba., Inc.

The formulations were prepared by combing the components of phase A in a beaker and heating with propeller agitation to about 80° C. until homogeneous. In a separate beaker, the components of phase B were combined and heated with propeller agitation to about 80° C. Phase B was then added to phase A, and was homogenized at 4000 RPM for about 3 minutes.

Homogenization was then ceased, and agitation was replaced with propeller mixing and the mixture was allowed to cool to about 50° C. at which time an emulsion was formed. The emulsion was poured off to canisters and allowed to cool to room temperature. The resulting viscosity for CA was 58,500. centipoise, and 39,000 centipoise for CB. The resulting pH for CA was 4.16, and 4.06 for CB.

Figure 10:
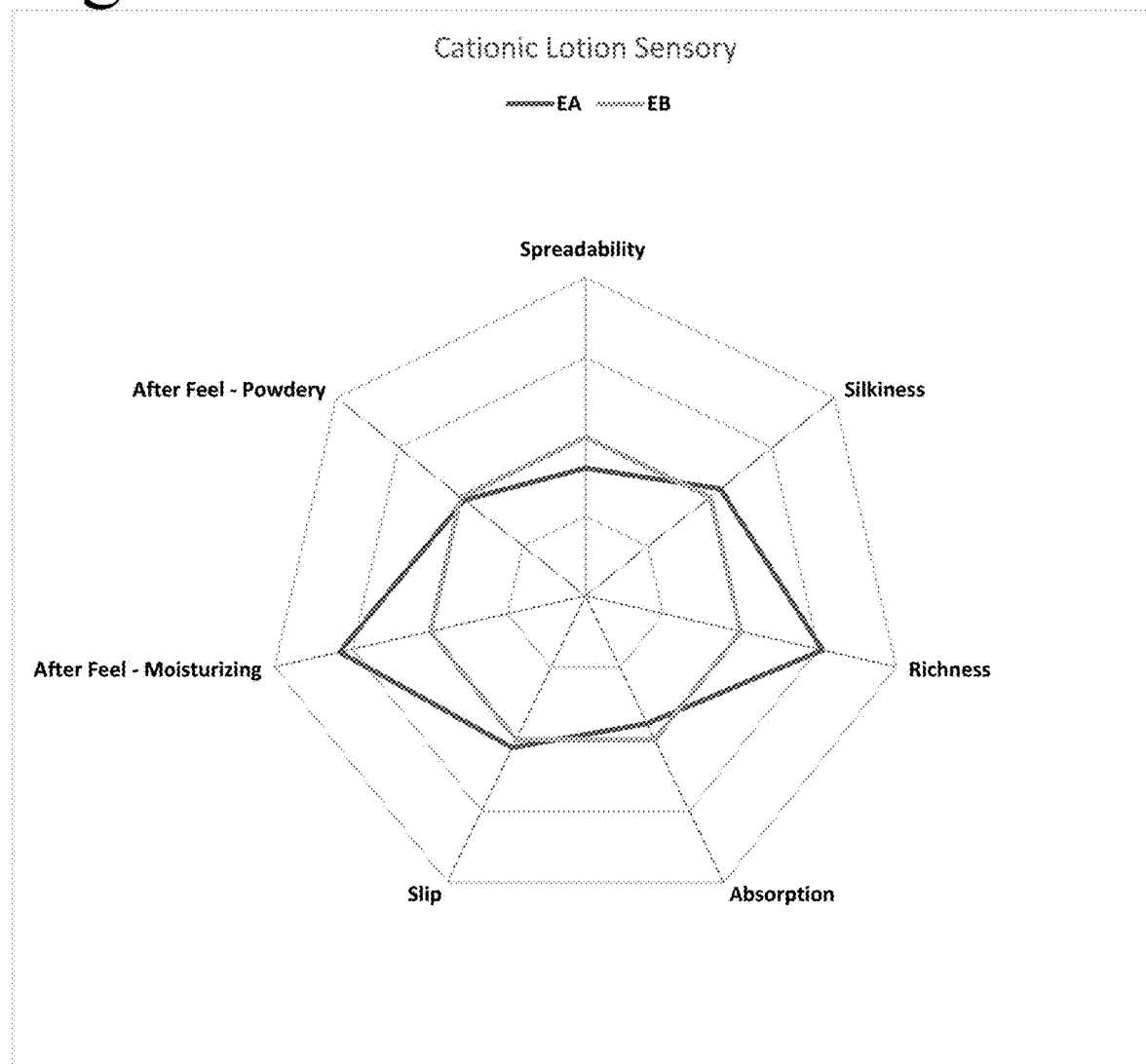
FIG. 10 is a graphic presentation of sensory data obtained from test panel.

The sensory properties of the emulsion were panel evaluated as described previously. The results are shown in the diagram of FIG. 10.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A homogeneous spreadable conditioning composition for use in a personal care formulation, the homogeneous spreadable conditioning composition consisting essentially of: a branched hydrocarbon having a total of X carbon atoms where X is an integer of 13 to 50 and in a concentration of 30% to about 70% by weight and an ester selected from the group consisting of: glyceryl triheptanoate, dicapryl succinate, heptyl undecylenate, and mixtures thereof in a concentration of about 20% to about 70% by weight;
   wherein each of the branched hydrocarbon and the ester are independently vegetable-derived;
   wherein the spreadable conditioning composition has a kinematic viscosity of less than or equal to about 100 centistokes; and
   wherein the spreadable conditioning composition has an average spreading velocity at 25° C. that is greater than that of the ester alone.

2. The homogeneous spreadable conditioning composition of claim 1, wherein each of the vegetable-derived branched hydrocarbon and the vegetable-derived ester are independently not derived from a palm oil.

3. The homogeneous spreadable conditioning composition of claim 1, wherein the branched hydrocarbon has at least 3 branches on a main hydrocarbon chain.

4. The homogeneous spreadable conditioning composition of claim 3, wherein the branched hydrocarbon has 4 or 5 branches on a main hydrocarbon chain.

5. The homogeneous spreadable conditioning composition of claim 1, wherein the branched hydrocarbon has 2 to 10 branches on a main hydrocarbon chain, the main hydrocarbon chain having Y carbon atoms and Y is an integer of 10 to 30 carbon atoms.

6. The homogeneous spreadable conditioning composition of claim 5, wherein X is 15 and Y is 12.

7. The homogeneous spreadable conditioning composition of claim 1, wherein the branched hydrocarbon is hydrogenated farnesene.

8. The homogeneous spreadable conditioning composition of claim 1, wherein the ester has 2, 3, 4, 5, or 6 ester linkages.

9. The homogeneous spreadable conditioning composition of claim 1, wherein the ester is selected from: glyceryl triheptanoate in a concentration of about 60% by weight, dicapryl succinate in a concentration of about 60% to about 70% by weight, and heptyl undecylenate in a concentration of about 30% by weight.

10. The homogeneous spreadable conditioning composition of claim 9, wherein the branched hydrocarbon is selected from a hydrocarbon having 15 to 20 carbon atoms in total and a main hydrocarbon chain of 12 carbon atoms, hydrogenated farnesene, farnesene, and mixtures thereof.

11. The homogeneous spreadable conditioning composition of claim 8, wherein the ester is present in a concentration of about 30% to about 60% by weight.

12. The homogeneous spreadable conditioning composition of claim 2, wherein the ester is derived from a vegetable source selected from the group consisting of: plants of genera *Pruna*, plants of family Arecaceae, coconut, almond, castor, corn, cottonseed, flax seed, hempseed, nut, olive, peanut, safflower, sesame, soybean, sunflower, jojoba, and combinations thereof.

13. The homogeneous spreadable conditioning composition of claim 1, wherein the branched hydrocarbon and the ester are present in a relative ratio selected from: about 2:about 3; about 1:about 2.5; about 1:about 1; and about 2.5:about 1, by weight.

14. The homogeneous spreadable conditioning composition of claim 1, exhibiting an average spreading velocity at 25° C. of about 4 cm$^2$/min to about 8 cm$^2$/min.

15. The homogeneous spreadable conditioning composition of claim 1, having a kinematic viscosity of less than or equal to about 25 centistokes.

16. The homogeneous spreadable conditioning composition of claim 15, wherein the branched hydrocarbon is hydrogenated farnesene and the ester is present in a concentration of about 30% to about 60% by weight.

17. A personal care formulation comprising the homogeneous spreadable conditioning composition of claim 1 and an ingredient selected from the group consisting of: a surfactant, a colorant, a detersive agent, a mechanical sunscreen, a fragrance, a chelator, an antioxidant, a UV absorbing compound, a particulate, a solvent, a cationic emulsifier, a nonionic emulsifier, an anionic emulsifier, an antimicrobial, and mixtures thereof.

18. A method of preparing a surface conditioning formulation comprising mixing the composition of claim 1 with an additional ingredient selected from a surfactant, a colorant, a detersive agent, a mechanical sunscreen, a fragrance, a chealtor, an antioxidant, a UV absorbing compound, a particulate and a solvent.

19. The method of claim 18, wherein the formulation contains only plant-derived ingredients.

20. The method of claim 19, wherein the formulation does not contain palm oil-derived ingredients.

21. A method of delivering a material to a surface comprising applying a formulation to the surface wherein the formulation comprises the homogeneous spreadable conditioning composition of claim 1 and an additional ingredient selected from a UV absorbing agent, a biologic, a patinator, an antimicrobial agent, an antioxidant, a mica, glitter, a pigment, an anti-rust agents, an anti-tarnish agent, a whitener, and a self-tanner.

22. The method of claim 21 wherein the surface is a surface of skin, fur, hair, nails or hooves.

23. The homogeneous spreadable conditioning composition of claim 14, having a kinematic viscosity of less than or equal to about 7 centistokes.

24. The homogeneous spreadable conditioning composition of claim 16, having a kinematic viscosity of less than or equal to about 7 centistokes.

* * * * *